United States Patent [19]

Cardillo et al.

[11] Patent Number: 5,527,693
[45] Date of Patent: Jun. 18, 1996

[54] PROCESS FOR THE PREPARATION OF SATURATED DELTA-DECANOLIDE OR DELTA-DODECANOLIDE BY BIOHYDROGENATION

[75] Inventors: Rosanna Cardillo; Claudio Fuganti, both of Milan; Massimo Barbeni; Gianna Allegrone, both of Turin, all of Italy

[73] Assignee: Pernod Ricard, Paris, France

[21] Appl. No.: 391,480

[22] Filed: Feb. 21, 1995

Related U.S. Application Data

[63] Continuation of Ser. No. 80,624, Jun. 22, 1993, abandoned.

[30] Foreign Application Priority Data

Jun. 22, 1992 [IT] Italy ................ TO92A0532

[51] Int. Cl.$^6$ ................ C12P 17/06; C12P 7/42; C12P 1/02
[52] U.S. Cl. ................ 435/125; 435/146; 435/171
[58] Field of Search ................ 435/125, 146, 435/171

[56] References Cited

FOREIGN PATENT DOCUMENTS

| 2025678 | 9/1990 | Canada . |
| 0412880 | 2/1991 | European Pat. Off. . |

*Primary Examiner*—John W. Rollins
*Assistant Examiner*—Francisco C. Prats
*Attorney, Agent, or Firm*—Jacobson, Price, Holman & Stern

[57] ABSTRACT

The production of natural delta-decanolide and/or delta-dodecanolide or mixtures thereof, by means of the biohydrogenation of a substrate containing the corresponding unsaturated lactones, delta-decen-2-olide and delta-dodecen-2-olide, respectively, and mixtures thereof, is performed by means of the use of a microorganism chosen from the group consisting of *Saccharomyces delbrueckii, Pichia ohmeri, Hansenula anomala, Pichia stipitis, Debaromyces hansenii, Zymomonas mobilis, Zygosaccharomyces rouxii, Schawnniomyces occidentalis, Sarcina lutea* and *Geotrichum candidum*.

7 Claims, No Drawings

PROCESS FOR THE PREPARATION OF SATURATED DELTA-DECANOLIDE OR DELTA-DODECANOLIDE BY BIOHYDROGENATION

This application is a continuation application of Ser. No. 08/080,624, filed Jun. 22, 1993, now abandoned.

The present invention relates to a process for the preparation of saturated delta-lactones, and especially delta-decanolide and/or delta-dodecanolide, by biohydrogenation of the corresponding natural unsaturated compounds using microorganisms.

Consumer preference for the use of natural flavouring agents as against synthetic ones has led to an investigation of natural methodologies that enable access to be gained to appreciable amounts of flavouring products which are not accessible at low cost by extraction from natural sources.

These methodologies comprise the enzymatic conversion of natural substances which are accessible at low cost to the desired substances which are present in traces in nature.

Such a procedure, termed bioconversion, has received special attention for the production of gamma- and delta-lactones containing from 6 to 12 carbon atoms. The processes of microbial beta-oxidation of the hydroxylated derivatives of natural fatty acids are especially effective. In this way, both gamma-decanolide and delta-decanolide can be isolated from fermentation processes in which unsaturated $C_{18}$ fatty acids containing a hydroxyl function at positions 12 and 13, respectively, are administered to a vast series of microorganisms; however, while the first precursor, ricinoleic acid, is abundant in nature, it is more difficult to gain access to the second, coriolic acid.

Patent Application EP-A-0,412,880 describes a process for the production of saturated or unsaturated gamma- or delta-lactones from substrates containing hydroxides or hydroperoxides of linoleic, linolenic or oleic acid, employing microorganisms capable of performing a beta-oxidation of the abovementioned hydroxides and hydroperoxides.

In particular, the abovementioned patent application describes the production of delta-decanolide, employing coriolic acid produced in the (S) form by lipoxygenation of linoleic acid followed by reduction of the intermediate hydroperoxide, or by photo- or autoxidation of the same acid or its derivatives followed by a reduction.

Canadian Patent Application 2,025,678 describes an alternative method for the production of gamma-decanolide and gamma-dodecanolide, by biocatalytic reduction of the corresponding unsaturated lactones employing yeasts or fungi.

In particular, this patent application describes the capacity of bakers' yeast (*Saccharomyces cerevisiae*) and of a series of fungi such as *Polyporus durus, Ischnoderma benzoinum, Bjerkandera adusta, Poria xantha* or *Pleurotus ostreatus* to convert delta-decen-2-olide to the corresponding saturated product by simple contact of the starting unsaturated lactone with the biomasses mentioned above, in the presence of an appropriate sugar for recycling the cofactor which, on becoming oxidised, supplies the hydrogen needed for reduction of the double bond.

The distinctive feature of this process stems from the fact that a natural product is used as substrate, extracted, for example, from the Massoia tree (*Cryptocaria massoia*).

In the natural extract, besides the unsaturated $C_{10}$ lactone, the unsaturated $C_{12}$ homologue is also present, which homologue undergoes a hydrogenation in the processes mentioned above to become the corresponding saturated $C_{12}$ lactone.

The process described above is not, however, fully satisfactory. When bakers' yeast is used, the ratio of yeast to unsaturated lactone is very high; in particular, the use of 9 g/liter of yeast (dry weight) for 10 mg of unsaturated lactone is mentioned. When successive additions of substrate are performed, for the same amount of yeast, limited amounts of saturated product are, in turn, isolated. In view of the high cost of the natural substrate, this fact constitutes a drawback from an economic standpoint. It has to be recognised that the large amount of biomass makes it difficult to isolate the product, and/or that the latter may be biodegraded by the yeast itself.

The biomass/unsaturated substrate ratios are more favourable when fungi are used as reduction biocatalysts. Concentrations of saturated product of up to 600 mg/liter are described but, on the other hand, the incubation times are much longer, up to 7 days, and the times for growth of the mycelium even extend to a few weeks.

The aim of the present invention is to improve the process described in the abovementioned patent application, by performing a selection of microorganisms which make it possible to work with small amounts of biomass, short incubation times and high substrate concentrations.

To this end, a subject of the present invention is a process for the production of delta-decanolide and/or delta-dodecanolide or mixtures thereof, by means of the biohydrogenation of a substrate containing the corresponding unsaturated lactones, delta-decen-2-olide, delta-dodecen-2-olide or mixtures thereof; this process is characterised in that the biohydrogenation is performed by means of the use of a microorganism chosen from the group consisting of *Saccharomyces delbrueckii, Pichia ohmeri, Hansenula anomala, Pichia stipitis, Debaryomyces hansenii, Zymomonas mobilis, Zygosaccharomyces rouxii, Schawnniomyces occidentalis, Sarcina lutea* and *Geotrichum candidum*, and special mention may be made of the strains *Saccharomyces delbrueckii* CBS 1146 now designated *Torulaspora delbrueckii, Pichia ohmeri* CBS 5367, *Hansenula anomala* now designated *Pichia anomala* CBS 110, *Pichia stipitis* CBS 5773, *Debaryomyces hansenii* CBS 767, *Zymomonas mobilis* ATCC 29191, *Zygosaccharomyces rouxii* CBS 732, *Schawnniomyces occidentalis* CBS 819, *Sarcina lutea* DSM 348 and *Geotrichum candidum* CBS 23376.

It is noted that cultures of the abovementioned microorganisms in a state of growth are capable of reducing the unsaturated lactone and its higher homologue, either in the pure state or as present in Massoia extract, to give the corresponding saturated compounds in molar yields of isolated product which reach 85%, with substrate concentrations which reach 1.5 g/liter and contact times of between 24 and 48 hours.

Typically, the microorganism is grown on MPGA solid medium (20, 5, 20, 15)* at 27°–30° C. This preparation is used to prepare the preinoculate in MPGA liquid medium for 24 hours; 50 ml of this preinoculate are used to inoculate, at a concentration of 10%, 300-ml flasks containing 50 ml of MPGA After 24–48 hours, delta-decen-2-olide (Massoia lactone), pure or in the form of Massoia extract or of a mixture of it with its higher homologue delta-dodecen-2-olide, or alternatively the latter in the pure state, is added at a concentration of 1–2 g/liter. The culture is kept stirring at 30° C. for 24–48 hours.

*concentrations of each component of MPGA medium: Malt, Peptone, Glucose and Agar.

At the time of addition of the substrate, an equimolar amount of beta-cyclodextrin may be added.

After the stated time, the culture is brought to pH 3 and the conversion products are recovered according to appropriate conventional techniques for this purpose, for example by extraction with an organic solvent, preferably methylene chloride or ethyl acetate.

The solvent is dried, for example using sodium sulphate, and evaporated and the residue is distilled under vacuum. The composition is determined by GLC analysis and, in some cases, quantitative analysis is performed by measuring the ratio of the conversion products to an internal standard added at the time of the extraction.

In this way, it is observed that biohydrogenation of the unsaturated lactones is complete in 24 hours in some cases, and in other cases the phenomenon is confirmed after a further 24 hours of contact.

The amount of biomass produced is fairly limited and, as such, does not create any problem of emulsion or loss of product during the recovery.

EXAMPLE 1

Cultures of *Debaryomyces hansenii* CBS 767, grown for three days on MPGA, are used to inoculate 50 ml of MPGA which, after 24 hours of growth at 27°–30° C. with stirring, serve to inoculate 500 ml of MPGA. After 48 hours of growth with stirring, 50 mg of Massoia lactone are added to 10 300-ml flasks containing 50 ml of culture. The cultures are kept stirring for 24 hours and, after this lapse of time, are combined, the pH is brought to 3 and three extractions with 50 ml of methylene chloride are performed. The dried organic phase is evaporated with a fractionating column and the residue is distilled under vacuum. 420 mg of distillate containing approximately 90% of delta-decanolide devoid of starting material are obtained.

When 75 and 100 mg, respectively, of unsaturated substrate are used for 50 ml of culture, an unsaturated/saturated ratio is observed on GLC analysis after 24 hours.

EXAMPLE 2

Cultures *Pichia ohmeri* CBS 5367, grown under conditions identical to those of Example 1, are treated with 0.75 and 1 g/liter, respectively, of Massoia lactone. After 24 hours of incubation, a complete reduction of the unsaturated compound and a recovery of 75% of the product were observed.

EXAMPLE 3

Cultures of *Hansenula anomala* CBS 110, grown in the same manner, treated with 500 mg/liter of Massoia oil (Robertet) containing the unsaturated $C_{10}$ lactone and its $C_{12}$ higher homologue, yield after 48 hours a mixture of products exclusively containing the saturated products delta-decanolide and delta-dodecanolide in the same ratios as those in which the corresponding unsaturated compounds were present.

EXAMPLE 4

Cultures of *Saccharomyces delbrueckii* CBS 1146, grown as in the preceding example, treated with 1 g/liter of Massoia lactone, yield after 24 hours of incubation an approximately 1:1 mixture of saturated and unsaturated products. On leaving for a further 24 hours, a complete saturation is observed and the product is isolated in a 70% yield.

EXAMPLE 5

Cultures of *Saccharomyces delbrueckii* CBS 1146, grown as in Example 1, are treated with Massoia lactone (1 g/liter) and beta-cyclodextrin (8 g/liter). After 24 hours, a complete saturation of the double bond is observed and the desired saturated product is finally isolated in an 82% yield.

EXAMPLE 6

The procedure is as in Example 5, but 2 g/liter of Massoia lactone and 8 g/liter of beta-cyclodextrin are added. After 24 hours of incubation, the ratio of saturated lactone to unsaturated lactone is measured, and equals 7:5. After 48 hours, the unsaturated compound disappeared completely, while the desired saturated compound appeared as the main component of the extraction mixture.

We claim:

1. A process for the production of delta-decanolide or delta-dodecanolide or mixtures thereof, comprising subjecting a substrate containing the corresponding unsaturated lactones, 2-decenoic acid, 5-hydroxy lactone or 2-dodecenoic acid, 5-hydroxy lactone, respectively, or mixtures thereof to biohydrogenation, said biohydrogenation being performed by adding a microorganism selected from the group consisting of *Saccharomyces delbrueckii* CBS 1146, *Pichia ohmeri* CBS 5367, *Hansenula anomala* CBS 110, *Pichia stipitis* CBS 5773, *Debaryomyces hansenii* CBS 767, *Zymomonas mobilis* ATCC 29191, *Zygosaccharomyces rouxii* CBS 732, *Schawnniomyces occidentalis* CBS 819, and *Sarcina lutea* DMS 348 to said substrate, and recovering said delta-decanolide or delta-dodecanolide or mixtures thereof.

2. The process according to claim 1, wherein the substrate is a Massoia extract.

3. The process according to claim 1 wherein a beta-cyclodextrin is added to the substrate in an equimolar amount relative to the unsaturated lactones.

4. The process according to claim 1, wherein the microorganism is selected from the group consisting of *Pichia ohmeri* CBS 5367, *Hansenula anomala* CBS 110, *Pichia stipitis* CBS 5773, *Debaryomyces hansenii* CBS 767, *Zymomonas mobilis* ATCC 29191, *Zygosaccharomyces rouxii* CBS 732, *Schwanniomyces occidentalis* CBS 819 and *Sarcina lutea* DMS 348.

5. The process according to claim 1, wherein the microorganism is selected from the group consisting of *Pichia ohmeri* CBS 5367, *Hansenula anomala* CBS 110 and *Debaryomyces hansenii* CBS 767.

6. The process according to claim 1, further comprising conducting the biohydrogenation for about 24–48 hours.

7. The process according to claim 1, wherein the concentration of the substrate is 1–2 g/liter.

* * * * *